US008691887B2

(12) United States Patent  
Ou-Yang

(10) Patent No.: US 8,691,887 B2
(45) Date of Patent: Apr. 8, 2014

(54) ANTIMICROBIAL COATING COMPOSITIONS

(75) Inventor: David Tien-Tung Ou-Yang, Woodbury, MN (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 34 days.

(21) Appl. No.: 12/476,997

(22) Filed: Jun. 2, 2009

(65) Prior Publication Data

US 2010/0137472 A1 Jun. 3, 2010

Related U.S. Application Data

(60) Provisional application No. 61/118,988, filed on Dec. 1, 2008.

(51) Int. Cl.
*C09D 5/14* (2006.01)
*C08K 3/10* (2006.01)
*C08K 3/28* (2006.01)
*C08K 3/34* (2006.01)
*C08K 5/05* (2006.01)
*C08K 5/07* (2006.01)
*C08K 5/13* (2006.01)
*C08K 9/04* (2006.01)

(52) U.S. Cl.
USPC .......... 523/122; 524/343; 524/354; 524/356; 524/379; 524/403; 524/429; 524/445; 524/492

(58) Field of Classification Search
USPC .......... 523/122; 524/343, 354, 356, 379, 403, 524/429, 445, 492; 428/411.1, 480
See application file for complete search history.

(56) References Cited

U.S. PATENT DOCUMENTS

| | | | |
|---|---|---|---|
| 3,223,629 A | 12/1965 | Loeffler | |
| 4,339,336 A | 7/1982 | Hammond et al. | |
| 4,584,192 A | 4/1986 | Dell et al. | |
| 4,629,743 A | 12/1986 | Hong | |
| 4,629,746 A | 12/1986 | Michl et al. | |
| 4,642,126 A | 2/1987 | Zador et al. | |
| 4,677,143 A | 6/1987 | Laurin et al. | |
| 4,716,032 A | 12/1987 | Westfall et al. | |
| 4,915,934 A | 4/1990 | Tomlinson | |
| 4,925,668 A | 5/1990 | Khan et al. | |
| 5,023,082 A | 6/1991 | Friedman et al. | |
| 5,512,199 A | 4/1996 | Khan et al. | |
| 5,547,662 A | 8/1996 | Khan et al. | |
| 5,616,338 A | 4/1997 | Fox, Jr. et al. | |
| 5,698,229 A * | 12/1997 | Ohsumi et al. | 424/604 |
| 5,773,487 A | 6/1998 | Sokol | |
| 5,861,440 A | 1/1999 | Gohla et al. | |
| 6,051,609 A | 4/2000 | Yu et al. | |
| 6,127,320 A | 10/2000 | van Ooij et al. | |
| 6,242,526 B1 * | 6/2001 | Siddiqui et al. | 524/555 |
| 6,248,811 B1 | 6/2001 | Ottersbach et al. | |
| 6,326,417 B1 | 12/2001 | Jia | |
| 6,337,357 B1 | 1/2002 | Fukunishi et al. | |
| 6,353,041 B1 | 3/2002 | Qian | |
| 6,413,539 B1 | 7/2002 | Shalaby | |
| 6,488,942 B1 | 12/2002 | Ingemann | |
| 6,492,445 B2 * | 12/2002 | Siddiqui et al. | 524/156 |
| 6,576,633 B1 | 6/2003 | Young et al. | |
| 6,861,060 B1 | 3/2005 | Luriya et al. | |
| 6,896,889 B2 | 5/2005 | Chevalier et al. | |
| 7,074,839 B2 | 7/2006 | Fansler et al. | |
| 7,098,256 B2 | 8/2006 | Ong et al. | |
| 7,179,849 B2 | 2/2007 | Terry | |
| 7,198,800 B1 | 4/2007 | Ko | |
| 7,232,540 B2 | 6/2007 | Gould et al. | |
| 7,261,925 B2 | 8/2007 | Nesbitt | |
| 7,407,707 B2 | 8/2008 | Gould et al. | |
| 7,462,401 B2 | 12/2008 | Halfyard et al. | |
| 7,494,339 B2 | 2/2009 | Dias et al. | |
| 7,498,367 B2 | 3/2009 | Qian | |
| 7,514,477 B2 | 4/2009 | Klare et al. | |
| 7,816,434 B2 | 10/2010 | Hackbarth et al. | |
| 8,034,455 B2 | 10/2011 | Wang et al. | |
| 8,227,050 B1 | 7/2012 | O'Neil | |
| 8,263,102 B2 | 9/2012 | Labrecque et al. | |
| 2001/0016589 A1 | 8/2001 | Modak et al. | |
| 2001/0056133 A1 | 12/2001 | Montgomery et al. | |
| 2002/0028751 A1 | 3/2002 | Lokkesmoe et al. | |
| 2002/0040092 A1 * | 4/2002 | Siddiqui et al. | 524/555 |
| 2002/0119111 A1 | 8/2002 | Kilgour et al. | |
| 2002/0144705 A1 | 10/2002 | Brattesani et al. | |
| 2003/0072781 A1 | 4/2003 | Pelerin | |
| 2003/0119932 A1 | 6/2003 | Al-Akhdar et al. | |
| 2003/0147932 A1 | 8/2003 | Nun et al. | |

(Continued)

FOREIGN PATENT DOCUMENTS

CN 1526771 A 9/2004
CN 101353545 A 1/2009

(Continued)

OTHER PUBLICATIONS

"ComfortCoat Hydrophilic Coating," DSM in Medical, http://www.dsm.com/en_US/medical/public/home/pages/product-coating-comfortcoat.jsp, Updated Jan. 11, 2013, Printed Apr. 22, 2013.

(Continued)

*Primary Examiner* — Kriellion Sanders
(74) *Attorney, Agent, or Firm* — Jeanne Lukasavage; Craig Metcalf; Kirton McConkie

(57) ABSTRACT

Antimicrobial compositions and methods are disclosed. The antimicrobial compositions are particularly useful in providing antimicrobial capability to a wide-range of medical devices. In one aspect, the invention relates to a mild solvent coating using acrylate-type mild solution coating. These compositions include rheological modifiers as necessary. The compositions also include antimicrobial agents, which may be selected from a wide array of agents. Representative antimicrobial agents include cetyl pyridium chloride, cetrimide, alexidine, chlorexidine diacetate, benzalkonium chloride, and o-phthalaldehyde. Additionally, the compositions comprise one or more suitable mild solvents, such as a low molecular weight alcohol, alkane, ketone, and combinations thereof.

19 Claims, No Drawings

(56) References Cited

U.S. PATENT DOCUMENTS

| | | |
|---|---|---|
| 2003/0162839 A1 | 8/2003 | Symington et al. |
| 2003/0170308 A1 | 9/2003 | Cleary et al. |
| 2004/0039349 A1 | 2/2004 | Modak et al. |
| 2004/0058829 A1 | 3/2004 | Hei et al. |
| 2004/0115477 A1 | 6/2004 | Nesbitt |
| 2004/0185296 A1 | 9/2004 | Mazzanti |
| 2004/0234475 A1 | 11/2004 | Lannibois-Drean et al. |
| 2005/0048005 A1 | 3/2005 | Stockel |
| 2005/0100580 A1 | 5/2005 | Osborne et al. |
| 2005/0176905 A1 | 8/2005 | Moon et al. |
| 2005/0265931 A1 | 12/2005 | Qian |
| 2006/0165751 A1 | 7/2006 | Chudzik et al. |
| 2006/0165903 A1 | 7/2006 | Mazzanti |
| 2006/0239954 A1 | 10/2006 | Sancho |
| 2006/0258780 A1 | 11/2006 | Chaussade et al. |
| 2007/0000407 A1 | 1/2007 | Leong |
| 2007/0112112 A1 | 5/2007 | Kerschner et al. |
| 2007/0112146 A1 | 5/2007 | Falk et al. |
| 2007/0141524 A1 | 6/2007 | Brennan et al. |
| 2007/0160547 A1 | 7/2007 | Duffy et al. |
| 2007/0166344 A1 | 7/2007 | Qu et al. |
| 2007/0203574 A1 | 8/2007 | McGrath et al. |
| 2007/0225179 A1 | 9/2007 | Schutz et al. |
| 2007/0275101 A1 | 11/2007 | Lu et al. |
| 2008/0026026 A1* | 1/2008 | Lu et al. .................. 424/405 |
| 2008/0075761 A1 | 3/2008 | Modak et al. |
| 2008/0161763 A1 | 7/2008 | Harding et al. |
| 2008/0182921 A1 | 7/2008 | Suh et al. |
| 2009/0110844 A1 | 4/2009 | Platzer et al. |
| 2009/0114327 A1 | 5/2009 | Breunig |
| 2009/0162530 A1 | 6/2009 | Nesbitt |
| 2009/0176907 A1 | 7/2009 | Subramanian et al. |
| 2009/0188559 A1 | 7/2009 | Nesbitt |
| 2009/0220739 A1 | 9/2009 | Chougule |
| 2010/0135949 A1 | 6/2010 | Ou-Yang |
| 2010/0136209 A1 | 6/2010 | Ou-Yang et al. |
| 2010/0137379 A1 | 6/2010 | Ou-Yang |

FOREIGN PATENT DOCUMENTS

| | | |
|---|---|---|
| DE | 4011867 A1 | 10/1991 |
| EP | 0 036 294 | 3/1981 |
| EP | 0 338 418 A1 | 4/1989 |
| EP | 0 379 271 A2 | 1/1990 |
| JP | 05-277434 | 10/1993 |
| JP | 08-209064 | 8/1996 |
| JP | 09-151262 | 6/1997 |
| JP | 09-157548 | 6/1997 |
| JP | 2000-178475 A | 6/2000 |
| JP | 2001-072438 A | 3/2001 |
| JP | 2002-282762 | 10/2002 |
| JP | 2003-342402 | 12/2003 |
| JP | 2004-043669 A | 2/2004 |
| JP | 2005-028209 A | 2/2005 |
| JP | 2005-520912 A | 7/2005 |
| JP | 2007-016096 A | 1/2007 |
| KR | 20020066429 A | 8/2002 |
| WO | 98/58690 | 12/1998 |
| WO | 9858989 | 12/1998 |
| WO | 99/32168 | 7/1999 |
| WO | 00/66189 | 11/2000 |
| WO | 2006056482 A1 | 6/2006 |
| WO | 2006/074666 A2 | 7/2006 |
| WO | 2006099358 A2 | 9/2006 |
| WO | 2007/095576 A2 | 8/2007 |
| WO | 2007/100653 A2 | 9/2007 |
| WO | 2007100776 A2 | 9/2007 |
| WO | 2008/014447 A2 | 1/2008 |
| WO | 2008/031601 A1 | 3/2008 |
| WO | 2008/128896 A2 | 10/2008 |
| WO | 2008132045 A2 | 11/2008 |

OTHER PUBLICATIONS

"Lubricent—Lubricious Hydrophillic Coatings for Medical Devices," Harland Medical Systems, http://www.harlandmedical.com/index.php/materials/lubricent.html, pp. 1-2, Printed Apr. 22, 2013.

"UV & EB Cure," Xiper Innovations, Inc., http://xiperinnovations.com/uv_eb_cure, Printed Apr. 22, 2013.

Cabot Corporation, "Using Silicas and Aluminas in Coatings,", www.cabot-corp.com/Silicas-And-Aluminas/Coatings, downloaded from the internet on Apr. 26, 2011.

McDonnell, G., Russell, A.D. Antiseptics and Disinfectants: Activity, Action, and Resistance. Clinical Microbiology Reviews, (1999) 12(1), pp. 149-179.

* cited by examiner

ANTIMICROBIAL COATING COMPOSITIONS

RELATED APPLICATIONS

This application claims priority to U.S. provisional patent application No. 61/118,988, filed Dec. 1, 2008, entitled "Antimicrobial Compositions and Methods for Medical Product Use," which application is incorporated herein by this reference.

BACKGROUND OF THE INVENTION

The present invention relates to antimicrobial compositions and methods for use of those compositions in various medical applications. One of the major challenges of modern medical treatment is control of infection and the spread of microbial organisms.

One area where this challenge is constantly presented is in infusion therapy of various types. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

The vascular access device commonly includes a Luer adapter to which other medical devices may be attached. For example, an administration set may be attached to a vascular access device at one end and an intravenous (IV) bag at the other. The administration set is a fluid conduit for the continuous infusion of fluids and pharmaceuticals. Commonly, an IV access device is a vascular access device that may be attached to another vascular access device, closes the vascular access device, and allows for intermittent infusion or injection of fluids and pharmaceuticals. An IV access device may include a housing and a septum for closing the system. The septum may be opened with a blunt cannula or a male Luer of a medical device.

When the septum of a vascular access device fails to operate properly or has inadequate design features, certain complications may occur. Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals.

Current vascular access devices prevent complications, such as infection resulting in CRBSIs, by providing a septum that functions properly during attachment and/or access of the vascular access device by other medical devices. Septa that function properly will act, in part, as infection barriers between the internal and external environments of the vascular access device during attachment and/or access by other medical devices. By functioning properly as infection barriers, septa minimize CRBSI's and other complications.

An IV access device may include a housing and a septum for closing the system. The septum may be opened with a blunt cannula or a male Luer of a medical device. A vascular access device may serve as a nidus of infection, resulting in a disseminated BSI (blood stream infection). This may be caused by failure to regularly flush the device, a non-sterile insertion technique, or by pathogens that enter the fluid flow path through either end of the path subsequent to catheter insertion. When a vascular access device is contaminated, pathogens adhere to the vascular access device, colonize, and form a biofilm. The biofilm is resistant to most biocidal agents and provides a replenishing source for pathogens to enter a patient's bloodstream and cause a BSI.

Over the last 35 years, it has been common practice to use a thermoplastic polyurethane solution as the carrier for antimicrobial coating. The solvent is usually tetrahydrofuran (THF), dimethylformamide (DMF), or a blend of both. Because THF can be oxidized very quickly and tends to be very explosive, an expensive explosion-proof coating facility is necessary. The harsh solvents will also attack most of the polymeric materials, including polyurethane, silicone, polyisoprene, butyl rubber, polycarbonate, polyvinyl chloride, PET, and acrylics. Therefore medical devices made with these materials can become distorted and/or form microcracks on their surfaces. Another issue with this coating is that it takes almost 24 hours for the solvent to be completely heat evaporated. Accordingly, conventional technology has persistent problems with processing and performance.

Another limitation is the availability of suitable antimicrobial agents for use in such coatings. One of the most commonly used antimicrobial agents used in coating medical devices is silver. Silver salts and silver element are well known antimicrobial agents in both the medical surgical industry and general industries. They are usually incorporated into the polymeric bulk material or coated onto the surface of the medical devices by plasma, heat evaporation, electroplating, or by conventional solvent coating technologies. These technologies are tedious, expensive and not environmentally friendly.

In addition, the performance of silver coating medical devices is mediocre at best. For example, it can take up to 8 hours before the silver ion, ionized from the silver salts or silver element, to reach certain efficacy as an antimicrobial agent. As a result, substantial microbial activity can occur prior to the silver coating even becoming effective. Furthermore, the silver compound or silver element has an unpleasant color, from dark amber to black.

Accordingly, there is a need in the art for improved compositions for providing antimicrobial capability to medical devices of various types, and particularly devices related to infusion therapy. There is also a need for improved methods of applying such antimicrobial coatings to medical devices.

BRIEF SUMMARY OF THE INVENTION

The present invention has been developed in response to problems and needs in the art that have not yet been fully resolved by currently available antimicrobial compositions and methods. Thus, these compositions and methods are developed to reduce complications, such as the risk and occurrence of CRBSIs, by providing improved antimicrobial compositions and methods.

In one aspect, the present invention includes a mild solvent acrylate-type coating that has antimicrobial properties. This coating is also suitable for use on medical devices, particularly intravascular access devices like needleless valves of the type described and discussed above. The medical devices to be coated are themselves comprised of polymeric substrates, such as polycarbonate (PC), polyurethane (PU), polyvinyl chloride (PVC), and acrylic. Their surfaces are then coated with the mild solvent acrylate-type coating, which contains an antimicrobial agent uniformly distributed throughout its matrix. The antimicrobial agent is able to diffuse through the matrix and kill microscopic organisms that come in contact with the coating's surface.

The formulations of this invention are an acrylate-type mild solvent coatings, which have good adhesion to numerous plastic surfaces (including PC, PU, PVC and acrylic). In some embodiments, the mild solvent is selected from one or more low molecular weight alcohols (e.g., ethanol and isopropanol), alkanes (e.g., pentane and heptanes), ketones (e.g., acetone), and combinations thereof. The solvent generally comprises 40% less of the overall solution.

In some embodiments, the coating can also be dried at about 60° C. for less than about 10 minutes. In one example, the formulation is comprised of alkyl acrylate or alkyl methacrylate-type polymer as the coating resin in one or more mild solvents (e.g., isopropanol), rheological modifiers, and antimicrobial agents. The nano- or micro-sized particles of the antimicrobial agents are uniformly and permanently distributed throughout the whole coating matrix.

The coating solution can be sprayed, wiped, dipped, or distributed by using other conventional coating methods to coat a substrate's surface. In certain embodiments it can then be dried at room temperature or at about 60° C. for about 10 minutes or less. The coatings are generally more efficacious than those of silver element or silver compounds that are commonly used in the IV access devices on the market. The coatings also have a pleasant light color or an even clear color.

DETAILED DESCRIPTION OF THE INVENTION

This detailed description of the invention provides additional description of each of the aspects of the invention summarized above.

As discussed above, the present invention comprises a mild solvent antimicrobial coating. The antibacterial solvent coating comprises an acrylate polymer or copolymer; a rheological modifier; and an antimicrobial agent. Generally the acrylate polymer or copolymer is selected from the group consisting of alkyl acrylates, alkyl methacrylates, alkyl hydroxyl(meth)acrylates, and alkyl methoxycinnamate acrylate. The alkyl group can have a carbon number from 0 to 22 (0 means hydrogen, 1 means methyl, 2 means ethyl, 3 means propyl etc.), but preferably a number from 0 to 6, and more preferably between 0 to 3.

In the compositions, the rheological modifier is generally selected from the group consisting of organic clay, castor wax, polyamide wax, polyurethane, and fumed silica. The rheological modifier may be present in the amount of from about 0.2% to about 30% of the dry weight of the coating. That is, the weight of the coating once the solvent has evaporated. In certain other embodiments, the rheological modifier is present in the amount of from about 0.2% to about 20% of the dry weight of the coating. In certain other embodiments, the rheological modifier is present in the amount of from about 0.2% to about 10% of the dry weight of the coating.

The antimicrobial agent is generally selected from the group consisting of aldehydes, anilides, biguanides, silver, silver compounds, bis-pheonols, and quaternary ammonium compounds. In certain instances, the antimicrobial agent is preferred to be selected from the group consisting of cetyl pyridium chloride, cetrimide, benzalkonium chlorides, alexidine, chlorexidine diacetate, and o-phthalaldehyde.

The antimicrobial agent may be present in the composition in the amount of from about 0.5% to about 50% of the dry weight of the coating. In other embodiments, the antimicrobial agent is present in the composition in the amount of from about 0.5% to about 30% of the dry weight of the coating. In certain other embodiments, the antimicrobial agent is present in the amount of from about 0.5% to about 20% of the dry weight of the coating. Finally, in certain preferred embodiments, the antimicrobial agent is present in the amount of from about 0.5% to about 7.0% of the dry weight of the coating.

As discussed above, in some embodiments, the formulations of this invention are mixed in a mild solvent before being applied to a medical device. While the mild solvent may comprise any solvent that is capable of dissolving the described acrylate polymer or copolymer, some suitable examples of the mild solvent include one or more low molecular weight alcohols, alkanes, ketones, and combinations thereof. Some examples of suitable low molecular weight alcohols comprise methanol, ethanol, propanol, isopropanol, and butanol. Because methanol evaporates relatively quickly, however, methanol may not be preferred in all embodiments. Instead, in some currently preferred embodiments, the alcohol comprises ethanol or isopropanol. Some suitable examples of suitable low molecular weight alkanes comprise pentane, hexane, heptane, and isomers thereof. Indeed, in some preferred embodiments the mild solvent comprises hexane or heptanes. Additionally, an example of a suitable low molecular weight ketone is acetone. However, in embodiments in which the solvent comprises acetone, the solvent preferably also comprises another mild solvent, such as an alcohol or an alkane.

The aforementioned solvents may be preferred for several reasons. In one example, the aforementioned solvents are gentler on medical devices that comprise PC, PU, PVC, or another similar material than are some conventional solvents (e.g., tetrahydrofuran (THF) and dimethyl formaldehyde (DMF)). In other words, the aforementioned solvents are less likely than some conventional solvents (e.g., THF and DMF) to distort or crack the medical devices to which they are applied.

In another, example, the aforementioned mild solvents may evaporate more quickly than other conventional solvents. Accordingly, the coating process is faster where aforementioned mild solvents are used. In still another example, the described mild solvent are less toxic and less explosive than certain other conventional solvents (e.g., THF and DMF).

As with the other disclosed compositions, the antimicrobial agents, which are uniformly distributed in the polymer matrix, gradually diffuse out of the matrix when the matrix is softened by the IV fluids or other types of fluids, and kill the microbes that come into contact with the coating surface.

The data from Table 1 shows the effectiveness of various compositions employing various antimicrobial agents. Each composition includes an acrylate polymer or copolymer, a rheological modifier, isopropanol, and the listed antimicrobial agent.

TABLE 1

The Contact Kill (%) of *S. epidermidis* by using different antimicrobial agents in the formulations.

| Antimicrobial Agents | Contact kill (%) S. Epidermidis 1 min. | Contact Kill (%) S. Epidermidis 1 hr. | Contact Kill (%) S. Epidermidis 8 hrs. |
|---|---|---|---|
| Chlorhexidine Diacetate | 4 | 30.1 | 100 |
| Chlorhexidine Gluconate | 0 | 22.1 | 13.3 |
| Chlorhexidine Dichloride | 22.3 | 17.6 | 18.1 |
| Chlorhexidine Acetate | ND | ND | ND |
| Alexidine | 100 | N/G* | N/G |
| Trichlocarbonilide | 17.7 | 25.7 | 89.2 |
| Triclosan | 30.0 | 0 | 18.1 |
| Chitosan | 28.6 | 30.9 | 0 |
| Carboxymethyl Chitosan | 5.7 | 29.4 | 10.8 |
| Silver Sulfadiazine | 10.9 | 36.8 | 69.9 |
| Silver Acetate | 18.3 | 24.3 | 100 |
| Silver Citrate Hydrate | 13.7 | 19.1 | 84.3 |
| Silver Protein | 26.9 | 14.7 | 74.7 |
| Cetrimide | 20.6 | 100 | N/G |
| Cetyl pyridium Chloride | 9.7 | 100 | N/G |
| Benzalkonium Chloride | 23.4 | 29.4 | 100 |
| Hexamethylene Tetramine | ND* | ND | ND |
| Chloroxylenol | 36.6 | 18.4 | 22.9 |
| o-phthalaldehyde | 19.4 | 100 | N/G |
| Bisphenol | 19.4 | 24.3 | 37.3 |
| HM-4100 | 20.6 | 18.4 | 28.9 |
| Hm-4072 | 21.7 | 18.4 | 69.9 |
| AGS-20 | 13.1 | 41.2 | 89.2 |

*1. NG = no growth (all microbes have been killed already)
*2. ND = no data

The following is a representative formulation within the scope of the present invention:

1. Acrylate copolymer solution, such as Lubrizol's Avalure AC-315, 20% by weight in isopropanol (Lubrizol Advanced Materials, Inc. Cleveland, Ohio);
2. Rheological modifier, such as Cabot's TS-720, 10% by weight of solid acrylate copolymer;
3. Antimicrobial agent, such as Alexidine or cetrimide or cetyl pyridium chloride, 7% by weight of solid acrylate copolymer.

The acrylate-type polymer, copolymer, or polymer resins should be soluble in one or more of the aforementioned mild solvents (e.g., common low molecular weight alcohols, such as methanol, ethanol, isopropanol, etc.; low molecule weight alkanes, such as pentane, heptane, hexane, etc.; and/or simple ketones, such as acetone. Preferably, the polymers should not dissolve in water. The polymer or copolymer can be alkyl acrylate, alkyl methacrylate, alkyl hydroxyl(meth)acrylate or alkyl methoxycinnamate acrylate and the like. Examples are Lubrizol's Avalure AC-315 and National Starch and Chemical Company's Dermacryl 79 (Bridgewater, N.J.).

The rheological modifiers can be organic clay, castor wax, polyamide wax, polyurethane, fumed silica, and the like. The quantity of the modifier can be less than 30% by dry weight of the mild solvent coating, preferably less than 20%, and most preferably between about 0.2% and about 10% dry weight of the mild solvent coating.

The antimicrobial agents can be aldehydes, anilides, biguanides, silver element or its compounds, bis-phenols, and quaternary ammonium compounds for the formulations. The preferred agents may be cetyl pyridium chloride, cetrimide, benzalkonium chloride, alexidine, chlorhexidine diacetate or o-phthalaldehyde. The quantity of the agent in the formulation should be less than 50% of the dry weight of the mild solvent coating, preferably less than 30%, and most preferably between about 0.5% and about 20%.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An infusion therapy medical device having an antimicrobial solvent coating comprising:
   an acrylate polymer or copolymer forming a matrix;
   an antimicrobial agent uniformly distributed in the matrix to gradually diffuse out of the matrix when the matrix is exposed to an IV fluid;
   a rheological modifier mixed with the acrylate polymer or copolymer and the antimicrobial agent; and
   a mild solvent mixed with the acrylate polymer or copolymer, the antimicrobial agent, and the rheological modifier, wherein the antimicrobial solvent coating comprises the rheological modifier in the amount of from about 0.2% to about 30% of the dry weight of the coating.

2. The device of claim 1, wherein the acrylate polymer or copolymer is selected from the group consisting of alkyl acrylates, alkyl methacrylates, alkyl hydroxyl (meth)acrylates, and alkyl methoxycinnamate acrylate.

3. The device of claim 1, wherein the rheological modifier is selected from the group consisting of organic clay, castor wax, polyamide wax, polyurethane, and fumed silica.

4. The device of claim 1, wherein the antimicrobial agent is selected from the group consisting of aldehydes, anilides, biguanides, silver, silver compounds, bis-phenols, and quaternary ammonium compounds.

5. The device of claim 1, wherein the antimicrobial agent is selected from the group consisting of cetyl pyridium chloride, cetrimide, benzalkonium chlorides, alexidine, chlorhexidine diacetate, and o-phthalaldehyde.

6. The device of claim 1, wherein the mild solvent is selected from the group consisting of low molecular weight alcohols, low molecular weight alkanes, simple ketones, and combinations thereof.

7. The device of claim 1, wherein the composition comprises the rheological modifier in the amount of from about 0.2% to about 20% of the dry weight of the coating.

8. The device of claim 1, wherein the composition comprises the rheological modifier in the amount of from about 0.2% to about 10% of the dry weight of the coating.

9. The device of claim 1, wherein the composition comprises the antimicrobial agent in the amount of from about 0.5% to about 50% of the dry weight of the coating.

10. The device of claim 1, wherein the composition comprises antimicrobial agent in the amount of from about 0.5% to about 30% of the dry weight of the coating.

11. The device of claim 1, wherein the composition comprises antimicrobial agent in the amount of from about 0.5% to about 7.0% of the dry weight of the coating.

12. An infusion therapy medical device having an antimicrobial solvent coating comprising:
    an acrylate polymer or copolymer forming a matrix;
    from about 0.5% to about 50% by dry weight an antimicrobial agent uniformly distributed in the matrix to gradually diffuse out of the matrix when the matrix is exposed to an IV fluid;

from about 0.2% to about 30% by dry weight a rheological modifier mixed with the acrylate polymer or copolymer and the antimicrobial agent; and a mild solvent mixed with the acrylate polymer or copolymer, the antimicrobial agent, and the rheological modifier.

13. The device of claim 12, wherein the acrylate polymer or copolymer is selected from the group consisting of alkyl acrylates, alkyl methacrylates, alkyl hydroxyl (meth)acrylates, and alkyl methoxycinnamate acrylate.

14. The device of claim 13, wherein the alkyl group has a carbon number from 1 to 22.

15. The device of claim 13, wherein the alkyl group has a carbon number from 1 to 3.

16. The device of claim 12, wherein the composition comprises the rheological modifier in the amount of from about 0.2% to about 10% of the dry weight of the coating.

17. The device of claim 12, wherein the composition comprises the antimicrobial agent in the amount of from about 0.5% to about 20% of the dry weight of the coating.

18. The device of claim 12, wherein the composition comprises antimicrobial agent in the amount of from about 0.5% to about 7.0% of the dry weight of the coating.

19. An infusion therapy medical device or a component of an infusion therapy medical device comprising an antimicrobial solvent coating comprising:

an acrylate polymer or copolymer forming a matrix and selected from the group consisting of alkyl acrylates, alkyl methacrylates, alkyl hydroxyl (meth) acrylates, and alkyl methoxycinnamate acrylate;

an antimicrobial agent uniformly distributed in the matrix and selected from the group consisting of a aldehydes, anilides, biguanides, silver, silver compounds, bis-phenols, and quaternary ammonium compounds, the antimicrobial agent gradually diffuses out of the matrix when the matrix is exposed to an IV fluid;

a rheological modifier mixed with the acrylate polymer or copolymer and the antimicrobial agent, the rheological modifier being selected from the group consisting of organic clay, castor wax, polyamide wax, polyurethane, and fumed silica; and a mild solvent mixed with the acrylate polymer or copolymer, the antimicrobial agent, and the rheological modifier, wherein the mild solvent is selected from the group consisting of a low molecular weight alcohol, a low molecular weight alkane, a simple ketone, and combinations thereof, wherein the composition comprises the rheological modifier in the amount of from about 0.2% to about 30% of the dry weight of the coating.

* * * * *